United States Patent [19]

Nowacki et al.

[11] Patent Number: 4,715,375

[45] Date of Patent: Dec. 29, 1987

[54] DEGASSIFICATION OF WATER IN HYDRAULIC SPARK GAP SHOCK WAVE GENERATOR

[75] Inventors: Christopher Nowacki, Arlington Heights; Alfred G. Brisson, Kildeer, both of Ill.

[73] Assignee: Trutek Research, Inc., Lake Zurich, Ill.

[21] Appl. No.: 928,524

[22] Filed: Nov. 7, 1986

[51] Int. Cl.[4] .................. A61B 17/22

[52] U.S. Cl. .................. 128/328; 367/147; 128/24 A

[58] Field of Search .................. 128/328, 24 A, 660; 367/147, 145; 181/106, 118, 120

[56] References Cited

U.S. PATENT DOCUMENTS 3,970,076 7/1976 Hepp et al. .................. 128/24.5

4,630,607 12/1986 Duinker et al. .................. 128/328

FOREIGN PATENT DOCUMENTS 90138 10/1983 European Pat. Off. .................. 128/328

*Primary Examiner*—Michael H. Thaler

*Attorney, Agent, or Firm*—Robert M. Wolters

[57] ABSTRACT

Kidney stones are disintegrated by extracorporeal apparatus generated shock waves. A reflector open at one end, has a liquid such as water therein and a resilient disphragm across the open end of the reflector. A spark gap is provided in the reflector, and a spark across this gap generates a shock wave and produces gas in the liquid. A flexible enclosure within the reflector about the spark gap isolates the spark gap from most of the liquid in the reflector. Gas formed as an incident to discharging a spark across the gap is removed from this enclosure.

4 Claims, 4 Drawing Figures

DEGASSIFICATION OF WATER IN HYDRAULIC SPARK GAP SHOCK WAVE GENERATOR

BACKGROUND OF THE INVENTION

Kidney stones, and also naturally-occurring stones in the bladder and the ureter can be exquisitely painful, and often require surgical relief. Excision or destruction of stones in the bladder and sometimes in the ureter can be relatively easily accomplished, but removal of stones from the kidney is a major procedure.

Removal of stones from the kidney is a very serious and traumatic surgical procedure. A large incision is made in the body. The kidney is essentially removed from the body and cut open. The stone or stones are then removed, whereupon the kidney is sutured and returned to the body, with the body then being sutured. Various efforts have been made to destroy or disintegrate kidney stones so that they can be excreted with the urine.

Chemotherapy is available as a non-invasive therapy for uric acid stones. In this therapy, the urine is alkalyzed, and the stone is dissolved over a substantial period of time. This requires detection of the stone before an acute phase is reached.

The next step was the use of ultrasound or an electrohydraulic shock wave produced by discharging a capacitor across a spark gap under water or other suitable liquid. Early efforts required invasion of the body, either through the urethra or through a surgical incision.

Subsequently, efforts have been made for the extracorporeal destruction of kidney stones through the use of a focused shock wave. In U.S. Pat. No. 3,942,531, for example, a reflector is used which is a portion of an ellipsoid. The spark gap is located at the first focus point of the ellipsoid, and the ellipsoid is positioned relative to the body so that the kidney stone or other calculus or concretion is at the second focus point of the ellipsoid. The reflector is filled with water. Discharge of a spark across the gap causes rapid vaporization of a portion of the water, and resultant generation of a shock wave which is focused by the reflector on the kidney stone. The shock wave travels through the water in the ellipsoidal reflector, and through the human tissues to the kidney stone. A repetition of the spark gap shock wave generation over a period of perhaps an hour, is necessary to destroy a kidney stone.

Repeated shock wave generation as just described results in an accumulation of gas within the water in the reflector. It has been found that the best approach to the human body is to have the patient lie on his back with the ellipsoidal reflector below him. This results in collection of gas at the interface between the water in the reflector and the body of the patient. This materially reduces energy transfer from the shock wave generator to the human body, and inhibits destruction of a kidney stone.

Simply replacing the water in the reflector has little effect in removing the gas, which tends to remain as an air bubble at the top of the reflector and beneath the diaphragm. This problem is exacerbated by a tendency of the gas to adhere to the underside of a diaphragm.

OBJECTS AND SUMMARY OF THE INVENTION

It is an object of the present invention to preclude the introduction of or generation of gas into the water filling a reflector in which a shock wave is generated by discharge of a spark across a spark gap.

More specifically, it is an object of the present invention to provide for shock wave generation by discharge of a spark across a spark gap in a reflector filled with water or the like wherein the spark gap is isolated from most of the water in the reflector so that gas generated by spark discharge is isolated from most of the water in the reflector and is readily removed.

In accordance with the present invention we provide an upwardly directed, truncated ellipsoidal reflector having the upper end covered with a flexible diaphragm of elastomeric or plastic resin material. The reflector is filled with water. A spark gap is provided at the first focus point of the reflector, and a spark generated across the gap causes vaporization of water to generate a shock wave. A small sack, bag or pouch surrounds the spark gap and supporting structure therefor, and isolates the water around the spark gap from the bulk of the water in the reflector. Gas generated by this spark gap thus accumulates within the bag. Water is circulated through the bag from the bottom up to a reduced apex, and out through a tube so that any gas generated will rise to the apex and be evacuated through the exhaust tube.

THE DRAWINGS

The present invention will best be understood from the following specification when taken in connection with the accompanying drawing wherein FIG. 1 is a longitudinal sectional view of the structure incorporating the present invention.

DETAILED DESCRIPTION OF THE ILLUSTRATED EMBODIMENTS

Figure 1:
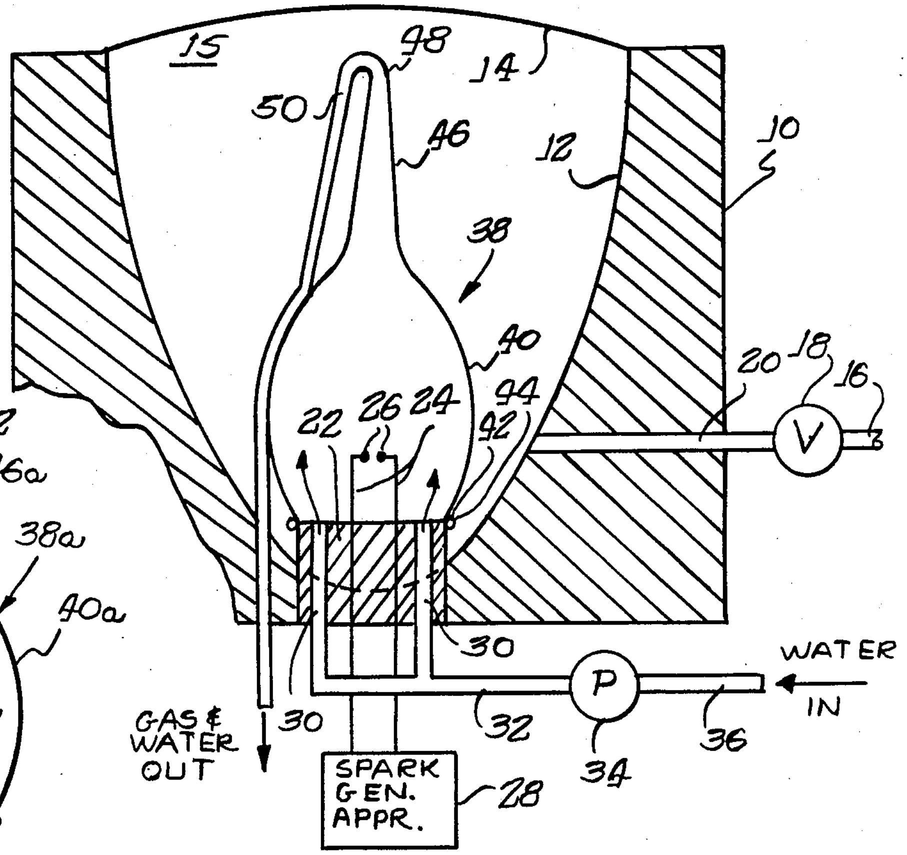
FIG. 1A is a detail of a modification of a portion thereof.

Directing attention first to FIG. 1, there will be seen a metal base or block 10 having a hollow interior in the form of an ellipsoidal reflector 12. A flexible diaphragm 14 is secured across the open top of the reflector 12 by any suitable means (not shown).

The diaphragm is waterproof as well as flexible, and preferably is made of an elastomeric or plastic resin material. An external water supply pipe 16 is connected to a valve 18 and a bore or channel 20 in the base to introduce water into the reflector 12, or to drain it, as the case may be.

An upstanding plug or pedestal 22 is provided extending upwardly through the bottom of the block into the reflector and supports electrical conductors 24 leading to a spark gap 26 at the first focus point of the ellipsoid of which the reflector 12 forms a portion. The electrical conductors 24 extend exteriorly of the base 10 through the plug 22, and are connected to suitable spark generating apparatus 28 such as a high voltage supply and a capacitor to be charged thereby and then discharged across the spark gap 26.

Vertical water inlet bores 30 extend upwardly through the plug 22, and are connected to a distribution pipe 32 which leads to a pump 34 receiving water from a pipe or the like 36. Water thus is circulated into the interior of the reflector 12, but in a restricted location as will be brought out immediately thereinafter.

A very thin, flexible resilient sack, bag, or pouch 38 is secured to the top of the pedestal or plug 22. This bag is somewhat in the nature of an upright balloon, and includes a bulbous ovoid, or egg-shaped lower portion 40. The lower portion 40 has an open lower end 42 encircling and secured to the upper end of the plug or pedestal 22 by suitable means such as a retaining band 44. The upper end of the bulbous section 40 opens into an elongated and upwardly directed funnel-like structure 46 tapering to an apex at 48. A length of tubing 50 is secured to the apex by suitable means such as an adhesive and extends down along the outside of the bag 38 and out through a bore in the base 10 for evacuation of gas and water.

Water pumped in by the pump 34 through the pipes or conduits 32 and 30 causes a slightly increased pressure within the bag 38, whereby to hold it in the upright, distended position shown. As a spark repeatedly jumps the spark gap 26 a certain amount of gas will be formed, but this will rise both gravitationally, and with the flow of water up into the funnel-shaped section 42 of the bag to the apex, and out through the tube 50. Thus, all gas generated by the spark is substantially immediately removed, and cannot under any circumstances come into contact with the inner or underface of the diaphragm 14 to inhibit the transfer of energy from the spark gap and reflector into a body positioned against the upper surface of the diaphragm 14. Tests have revealed that the energy transferred to the body above the diaphragm 14 is affected very little or not at all by the provision of the bag 38. Thus, the provision of the bag performs a useful feature of eliminating gas that might collect beneath the diaphragm without noticeably reducing the transfer of energy from the spark gap to the patient. It will be best understood that the patient or body disposed above the diaphragm 14 has a kidney stone that is located by suitable aiming means (not shown) so that the kidney stone lies at the second focus point of the reflector 12.

Figure 1A:
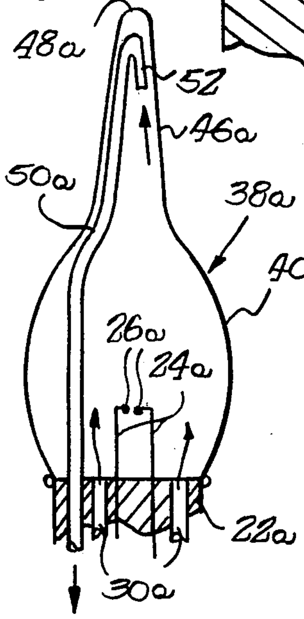

A modification of the invention is shown in FIG. 1A. The reflector is omitted from the drawing in this case along with the base 10 and the diaphragm. The fragmentary part of the invention illustrated is similar to the parts heretofore shown and described in connection with FIG. 1, and like parts are identified by similar numerals with the addition of the suffix a. The sack, bag or pouch **38*a* remains the same as previously illustrated, except that the apex 48*a* is sealed rather than opening directly into the exhaust tube. The exhaust tube 50*a* is contained entirely within the bag and extends upwardly to a position adjacent the apex 48*a* and has a downwardly turned entering or receiving end 52** for evacuating gas and water.

Figure 2:
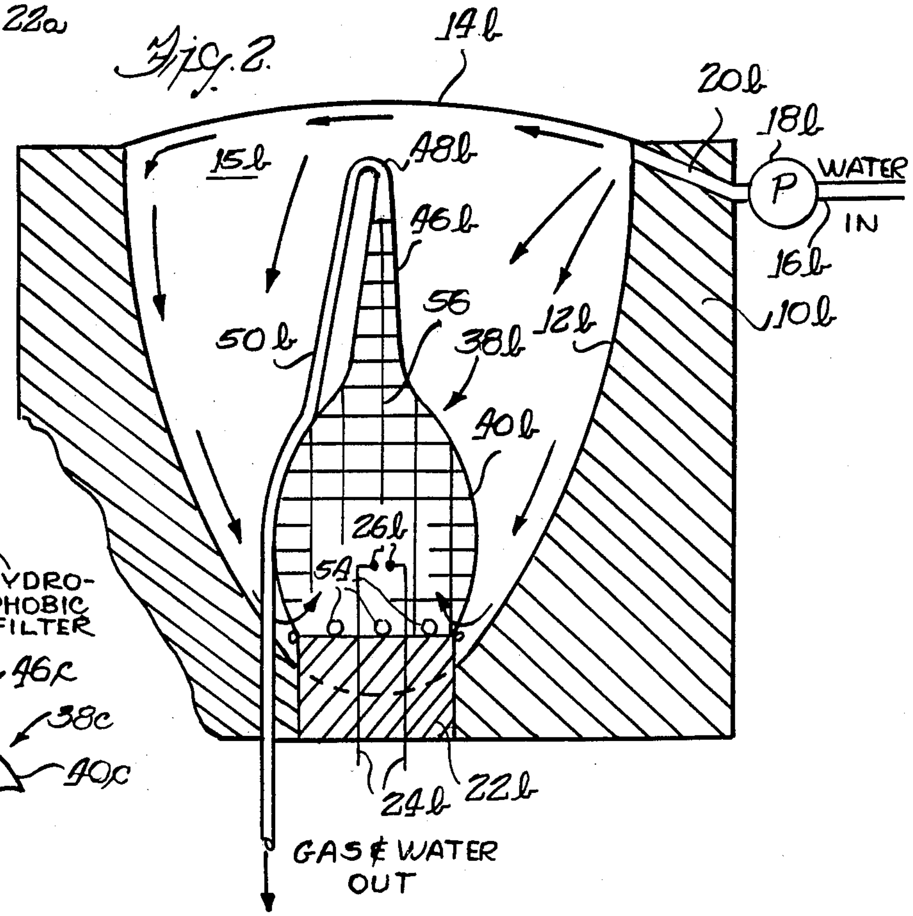
FIG. 2 is a view similar to FIG. 1 showing a different embodiment of the invention.

A further modification of the invention is shown in FIG. 2, the parts therein being identified by similar numerals with the addition of the suffix b. In this instance, water is continuously circulated into the reflector **12*b* by means of a pump 18*b* connected to an inlet pipe 16*b*. The conduit or passageway through the base 10*b* is generally adjacent the top of the base and is angled upwardly and inwardly relative thereto, so that some of the inlet water exiting therefrom will skim along the underside of the diaphragm 14*b* to pick up and clear away any gas that might inadvertently have entered the reflector 12*b* with the water pumped in. Water is not pumped directly into the sack, bag or pouch 38*b* as in FIG. 1. The bag is secured to the top of the pedestal 22*b*, as heretofor, and is provided with peripherally spaced inlet orifices 54 through which water from the reflector passes into the bag 38*b*. This water then passes up through the bag and out through the tube 50*b*, carrying with it any gas generated by the spark recurring in the spark gap 26*b*. No pressure is generated within the bag 38*b* any greater than the pressure within the reservoir 12*b*, and there therefor might be a tendency for the bag to collapse. Accordingly, a frame or cage 56 conforming to the shape of the bag 38*b* is provided within the bag to hold the bag in extended position as shown. The cage 56** comprises crossed supporting members and conveniently is made of plastic for ease of fabrication and for corrosion resistance. However, it could be made of non-corrosive wire, welded or soldered at the crossover points, or made of expanded metal by techniques well known in the art.

Figure 3:
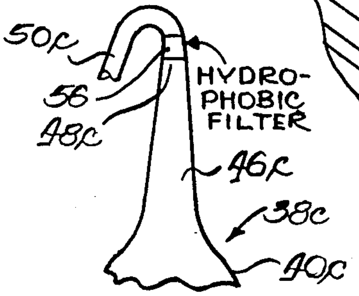
FIG. 3 is a fragmentary sectional view similar to a portion of FIG. 1 showing yet another modification.

A further embodiment of the invention is fragmentarily illustrated in FIG. 3. Like parts in this instance are identified by similar numerals with the addition of the suffix c. The distinction in this case is that a hydrophobic filter 56 is secured at the apex **48*c* and at the inlet to the tubing 50*c*. Accordingly, only a minimum of water need be pumped into the bag 38*c***, since only gas and substantially no water will pass through the hydrophobic filter.

In each embodiment of the invention as now shown and described, the spark gap is isolated from most of the water in the ellipsoidal reflector, and particularly from that water which is in contact with the diaphragm at the otherwise open top of the reflector. Thus, gas that is generated by sparks jumping the gap cannot collect beneath the diaphragm to inhibit energy transfer. The gas so generated is circulated out of the system through the exhaust tubing at the top of the bag on a continuous basis. A test apparatus constructed in accordance with the invention as herein shown and described, has proved remarkably effective at degassification of water in the hydraulic spark gap shock wave generator with substantially no reduction in energy transferred to the body contacting the diaphragm 14, and ultimately the target kidney stone.

The various embodiments of the invention as herein shown and described are for illustrative purposes only. Various changes in structure will no doubt occur to those skilled in the art, and will be understood as forming a part of the present invention insofar as they fall within the spirit and scope of the appended claims.

I claim:

1. Apparatus for generating a shock wave comprising an upwardly opening reflector having its vertex at the lowest portion and opposite the open end, a resilient diaphram across the open end of the reflector, said reflector having a liquid such as water therein, means providing a spark gap in said reflector spaced up from said vertex, a spark across said gap causing a shock wave and producing gas in said liquid, and a flexible enclosure within said reflector upstanding from and adjacent the vetex thereof and substantially completely enclosing said spark gap means, said flexible enclosure being filled with a liquid such as water and isolating said spark gap means from most of the water in said reflector, said enclosure having a volume less than substantially one-half the volume of said reflector, and means for removing from said enclosure gas formed as an incident to discharging a spark across said gap, said diaphram being adapted to be pressed against a living body, and the liquid in said flexible enclosure and in said reflector coupling said shock wave through said diaphram to said living body, enclosure comprising an inverted bag supported by liquid therein, the bag tapering upwardly to an apex, the means for removing gas from the enclosure comprising exhaust means communicating with the interior of the bag adjacent said apex.

2. Apparatus as set forth in claim 1, and further including a support for said bag in said bag.

3. Apparatus as set forth in claim 1 wherein the gas removing means further comprises means for flowing liquid into said bag adjacent the bottom thereof and for flowing gas and liquid out adjacent said apex.

4. Apparatus as set forth in claim 1 wherein the means for removing gas from the enclosure includes a hydrophobic filter.

* * * * *